United States Patent
Obwolo et al.

(10) Patent No.: US 12,285,511 B2
(45) Date of Patent: Apr. 29, 2025

(54) PERFUME PROLONGER

(71) Applicant: Hart & Liberty Group Ltd., Leeds (GB)

(72) Inventors: Patricia Obwolo, Horley (GB); John Stephen, Cheltenham (GB)

(73) Assignee: Hart & Liberty Group Ltd., Leeds (GB)

( * ) Notice: Subject to any disclaimer, the term of this patent is extended or adjusted under 35 U.S.C. 154(b) by 826 days.

(21) Appl. No.: 17/602,979

(22) PCT Filed: Apr. 9, 2020

(86) PCT No.: PCT/IB2020/053386
§ 371 (c)(1),
(2) Date: Oct. 11, 2021

(87) PCT Pub. No.: WO2020/212809
PCT Pub. Date: Oct. 22, 2020

(65) Prior Publication Data
US 2022/0110849 A1 Apr. 14, 2022

(30) Foreign Application Priority Data
Apr. 15, 2019 (GB) .................................... 1905309

(51) Int. Cl.
*A61Q 13/00* (2006.01)
*A61K 8/34* (2006.01)
*A61K 8/37* (2006.01)
*A61K 8/49* (2006.01)

(52) U.S. Cl.
CPC .............. *A61K 8/4973* (2013.01); *A61K 8/34* (2013.01); *A61K 8/37* (2013.01); *A61Q 13/00* (2013.01)

(58) Field of Classification Search
CPC .......... A61K 8/4973; A61K 8/34; A61K 8/37; A61K 2800/591; A61Q 13/00

USPC ........................................................ 512/2, 1
See application file for complete search history.

(56) References Cited

U.S. PATENT DOCUMENTS

| | | | |
|---|---|---|---|
| 5,120,709 A * | 6/1992 | Cella | A61Q 13/00 512/2 |
| 2009/0176690 A1 | 7/2009 | Laudamiel et al. | |
| 2014/0127335 A1 | 5/2014 | Miller et al. | |

FOREIGN PATENT DOCUMENTS

| EP | 1201738 A1 | 5/2002 |
|---|---|---|
| WO | 2017/144093 A | 8/2017 |
| WO | 2017/190035 A | 11/2017 |

OTHER PUBLICATIONS

McGinty et al, Fragrance material review on w-pentadecalactone, 2011, Food and Chemical Toxicology, 49, 5192-5201 (Year: 2011).*
Search Report for counterpart Great Britain Application No. GB1905309.9 dated Aug. 29, 2019.
International Preliminary Report on Patentability for corresponding PCT Application No. PCT/IB2020/053386 dated Jul. 29, 2021.
Ayuob, "Evaluation of the antidepressant-like effect of musk in an animal model of depression: how it works", Anat Sci Int (2017) 92:539-553.
Mcginty et al., "Fragrance material review on ω-pentadecalactone", Food and Chemical Toxicology 49 (2011) S193-S201.

* cited by examiner

*Primary Examiner* — Jessica Whiteley
(74) *Attorney, Agent, or Firm* — Wood, Phillips, Katz, Clark & Mortimer

(57) ABSTRACT

A composition for application to the skin or other substrate, which acts in conjunction with any perfume product, to extend the longevity of a fragrance, compared to the perfume in the absence of the composition. In particular, the composition contains a musk substance and at least 50% of a non-scented, viscous, low-volatility, solvent for perfume ingredients.

14 Claims, No Drawings

PERFUME PROLONGER

BACKGROUND OF THE INVENTION

This invention relates to a perfume prolonger and in particular, to a composition which acts to enhance the longevity of a fragrance.

Perfumes are created from fragrance ingredients that are combined to produce a formulation with a desired strength and character. The ingredients are blended by a perfumer to achieve a fragrance that is desirable to the target audience. Aromatic materials are used having various volatilities which, for practical purposes are split into three main groups known as top notes, middle notes and base notes. Top notes are produced by small, light molecules that evaporate quickly. They deliver the initial impression of the perfume and are perceived as fresh and light. Middle notes are slightly more tenacious and emerge just prior to dissipation of the top notes. Base notes, such as woody, amber or musky scents, are the most tenacious and emerge in what is known as the 'dry out' or the final stage of evaporation of the fragrance. They are produced by large, heavy molecules that evaporate slowly.

The relative volatility of fragrance ingredients will determine the tenacity and therefore the rate of evaporation and the release of the fragrance. When creating a perfume, it is therefore also important to take into account volatility, in order to achieve a formulation which has the ability to deliver the desired character perceived by the nose.

In the past, users had to accept that a perfume having a light and delicate character has low tenacity and therefore the effect of the perfume does not last long. The only practical solution was to apply the fragrance more frequently.

Previous attempts to increase longevity of a perfume have involved adding so-called fixatives to the fragrance formulation, which slow the evaporation of the mixture from skin and other substrates. Often, however, the nature or quantity of a fixative is limited by the odour of the fixative itself. For example, the amount of fixative material that can be incorporated into the formulation may be limited by the need to avoid the scent associated with the fixative becoming noticeable if used at too high a level.

There is a need for a method of improving the longevity of a perfume formulation which does not affect the character of the perfume. It has now been found that the longevity and perception of a perfume can be enhanced by the separate application of a composition containing a viscous solvent and a musk. The composition has the added advantage that its effect is not limited to a specific perfume formulation. It can act in conjunction with any perfume product, enabling users to extend the longevity of their selected fragrance, yet retain the perception of the fragrance in the nose.

Prior compositions are known, sometimes referred to as fragrance primers, which are described as being used in combination with fragrances to make them longer lasting.

For example, US 2009/0176690 discloses a fragrance primer composition that contains a large array of existing fragrances. Although a musky ingredient is described, the document does not suggest a non-scented primer composition.

Primer compositions are also described in WO2017/190035, WO2017/144093 and US2014/0127335, but none disclose the presence of a musk.

U.S. Pat. No. 5,120,709 describes a method for enhancing the quality of an applied fragrance by separately applying a composition consisting of a fixative agent, which may be a musk. However, there is no disclosure of a low-volatility solvent. Indeed, the solvent is specified to be volatile.

BRIEF SUMMARY OF THE INVENTION

Although viscous or oily solvents and musk ingredients have previously been incorporated into perfume formulations, they have not been used in a separate composition in the absence of other fragrance materials to display the effects of the present composition.

Accordingly, the present invention provides a non-scented composition for application to the skin or other substrate, either prior to, or subsequent to, a perfume, which composition comprises a musk substance and at least 50% of the composition comprises a non-scented, viscous, low-volatility, solvent for perfume ingredients.

The composition of this invention is absent any other fragrance materials.

In particular the invention provides a composition for application to the skin or other substrate, which composition increases the intensity of the perfume five hours after application of the perfume by at least 10% compared to the intensity of the perfume in the absence of said composition.

Suitably, the increase in intensity of the perfume after five hours is at least 25%, for example at least 50%, preferably at least 75%.

The composition of this invention comprises at least 50% of a non-scented, viscous, low-volatility, solvent for perfume ingredients. Suitably, the solvent comprises at least 60%, preferably at least 70%, for example at least 80% of the composition.

The solvent has a viscous or oily character, but may not be non-polar. Its function is to dissolve the ingredients of a subsequently-, or previously-applied perfume, which is a complex mixture of polar and non-polar materials. A preferred solvent for incorporation into the composition of this invention therefore comprises a chemical compound having both polar and non-polar moieties.

The further function of the solvent is to retain a subsequently-applied, or previously-applied perfume onto the skin or other substrate and reduce the evaporation of perfume ingredients. For this reason, the solvent should be viscous and have a low volatility. Preferably the solvent in the composition of this invention has a vapour pressure of less than 0.3 Torr (40 Pa) at 25° C. The viscosity of the solvent is suitably greater than that of water, which is 1 centipoise (or 1 mPa) at 20° C. Preferably the solvent has a viscosity greater than 5 centipoise at 20° C.

The composition of this invention, as well as the solvent for incorporation into the present composition is non-scented. The term non-scented is used to mean compositions and solvents having sufficiently little scent to not substantially change the odour of the fragrance that is subsequently or previously applied to the skin or other substrate. Thus, the composition of this invention can be used in conjunction with any perfume, without affecting its character.

Preferably, the solvent does not leave a sticky feel when applied, especially when to substrate to which it is applied is human skin or hair. When the composition of this invention is to be applied to the skin, the solvent should be one that is safe to put on the skin.

The solvent may be hydrophobic or water miscible. Examples of suitable solvents for incorporation into the composition of this invention include diethyl phthalate, isopropyl myristate, dimethyl adipate, dimethyl succinate, dimethyl glutarate, triethyl citrate, acetyl triethyl citrate, acetyl tributyl citrate, benzyl benzoate, diethylene glycol monoethyl ether, 3-methoxy-3-methyl-1-butanol, 2-(2-ethoxyethoxy)-1-ethanol, monopropylene glycol, dipropylene glycol and isopropylidene glycerol.

Preferred solvents are diethyl phthalate, isopropyl myristate, monopropylene glycol, and dipropylene glycol. A particularly preferred solvent is diethyl phthalate.

The solvent may also be a natural oil such as jojoba oil, grape oil, wheatgerm oil, almond oil, rapeseed oil.

The other ingredient of the composition of this invention is a musk substance. A musk substance is a substance which has a musk-like odour. It includes natural animal extracts, isolated compounds that are the active principles of the natural musk odour, as well as synthetic compounds which emulate the musk odour.

A natural musk may be employed, such as deer musk. Alternatively, the musk substance may be a compound isolated from an animal extract, such as muscone.

However, it is preferred to use a synthetic musk. Many such compounds are known in the art. For the present invention, any compound which exhibits a musk-like odour may be incorporated into the composition. Known classes of synthetic musk substances include macrocyclic lactones, especially $C_{14}$-$C_{18}$ macrocyclic lactones, macrocyclic ketones, especially $C_{14}$-$C_{18}$ macrocyclic ketones, nitro musks, indanes, cyclic ethers, aliphatic lactones, polycyclic lactones, alicyclic musks and hydronaphthalenes.

Specific musk substances include the following, where CAS is the Chemical Abstracts Service number:

Macrocyclic Lactones

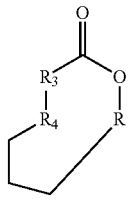

Omega-Pentadecalactone

R is —$CH_2$—$)_9$—
$R_3$-$R_4$ is —$CH_2$—$CH_2$—
CAS 106-02-5

(3E)-1-oxacyclohexadec-3-en-2-one

R is —($CH_2$)$_9$—
$R_3$-$R_4$ is —CH=CH—
CAS 34902-57-3

(12E)-1-oxacyclohexadec-12-en-2-one

R is —($CH_2$)$_3$—CH=CH—
$R_3$-$R_4$ is —($CH_2$)$_6$—
CAS 111879-80-2

1,7-dioxacycloheptadecan-8-one

R is —($CH_2$)$_5$—O—($CH_2$)$_4$—
$R_3$-$R_4$ is —$CH_2$—$CH_2$—
CAS 3391-83-1

1,4-dioxacyclohexadecane-5,16-dione

R is —$CH_2$—$CH_2$—O—(CO)—($CH_2$)$_5$—
$R_3$-$R_4$ is —$CH_2$—$CH_2$—
CAS 54982-83-1

1,4-dioxacycloheptadecane-5,17-dione

R is —$CH_2$—$CH_2$—O—(CO)—($CH_2$)$_6$—
$R_3$-$R_4$ is —$CH_2$—$CH_2$—
CAS 105-95-3

(10Z)-13-methyl-1-oxacyclopentadec-10-en-2-one

R is —($CH_2$)$_2$—CH($CH_3$)—$CH_2$—CH=CH—($CH_2$)$_2$—
$R_3$-$R_4$ is —$CH_2$—$CH_2$—

(8Z)-1-oxacycloheptadec-8-en-2-one

R is —($CH_2$)$_5$—CH=CH—
$R_3$-$R_4$ is —$CH_2$—$CH_2$—
CAS 123-69-3

(15S)-15-methyl-oxacyclohexadecan-2-one

R is —$CH_2$—CH($CH_3$)—($CH_2$)$_7$—
$R_3$-$R_4$ is —$CH_2$—$CH_2$—

Macrocyclic Ketones

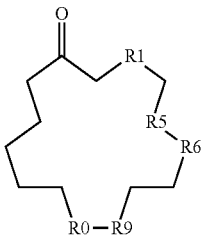

Cyclopentadecanone $R^1$ is —$CH_2$—
$R_5$-$R_6$ is —$CH_2$—$CH_2$—
$R_9$-$R_0$ is —$CH_2$—$CH_2$—
CAS 502-72-7

3-methylcyclopentadecanone $R^1$ is —CH($CH_3$)—
$R_5$-$R_6$ is —$CH_2$—$CH_2$—
$R_9$-$R_0$ is —$CH_2$—$CH_2$—
CAS 541-91-3

(9Z)-cycloheptadec-9-en-1-one $R^1$ is —$CH_2$—
$R_5$-$R_6$ is —$CH_2$—$CH_2$—
$R_9$-$R_0$ is —CH=CH—($CH_2$)$_2$—
CAS 542-46-1

3-methylcyclopentadec-5-en-1-one $R^1$ is —CH($CH_3$)—
$R_5$-$R_6$ is —CH=CH—
$R_9$-$R_0$ is —$CH_2$—$CH_2$—
CAS 63314-79-4

Nitro Musks

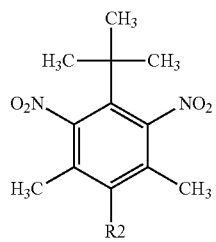

1,3-Dimethyl-5-(2-methyl-2-propanyl)-2,4,6-trinitrobenzene $R^2$ is —$NO_2$
CAS 81-15-2 (Musk Ketone)

1-[2,6-Dimethyl-4-(2-methyl-2-propanyl)-3,5-dinitrophenyl]ethenone $R^2$ is —$COCH_3$
CAS 81-14-1

Indanes

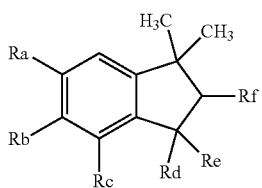

1-(1,1,2,3,3,6-hexamethyl-2H-inden-5-yl)ethenone

Ra is —$COCH_3$
Rb is —$CH_3$
Rc is —H
Rd is —$CH_3$; Re is —$CH_3$; Rf is —$CH_3$
CAS 125323-35-0

1-(6-tert-butyl-1,1-dimethyl-2,3-dihydro-1H-inden-4-yl)ethenone

Ra is —$C(CH_3)_3$
Rb is —H
Rc is —$COCH_3$
Rd is —H; Re is —H; Rf is —H
CAS 1371-00-1

1-(3-Isopropyl-1,1,2,6-tetramethyl-2,3-dihydro-1H-inden-5-yl)ethenone

Ra is —$CH_3$
Rb is —$COCH_3$
Rc is —H
Rd is —$CH(CH_3)_2$
Re is —H
Rf is —$CH_3$
CAS 68140-48-7

Hydroindanes

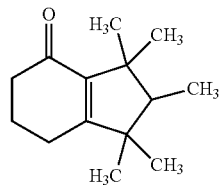

1,1,2,3,3-Pentamethyl-1,2,3,5,6,7-hexahydro-4H-inden-4-one

CAS 33704-61-9

Cyclic Ethers

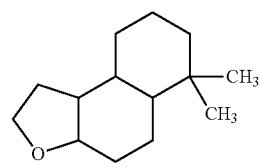

3a,6,6,9a-Tetramethyldodecahydronaphtho[2,1-b]furan

CAS 100679-85-4

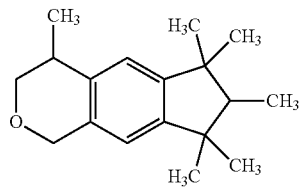 [SMILES: CC1COCc2cc3c(cc21)C(C)(C)C(C)C3(C)C]

4,6,6,7,8,8-Hexamethyl-1,3,4,6,7,8-hexahydrocyclopenta[g]isochromene

CAS 1222-05-5

Aliphatic Lactones

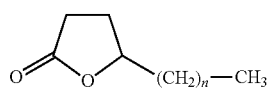

γ-decalactone n is 5
CAS 706-14-9

γ-dodecalactone n is 7
CAS 69830-92-8

Polycyclic Lactones

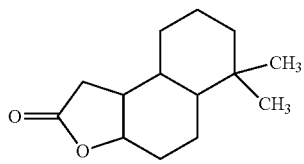 [SMILES: CC1(C)CCCC2C3CC(=O)OC3CCC21]

3a,6,6,9a-Tetramethyldecahydronaphtho[2,1-b]furan-2(1H)-one

CAS 564-20-5

Hydronaphthalenes

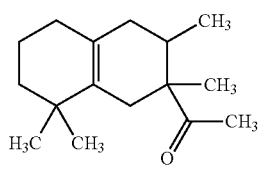 [SMILES: CC(=O)C1(C)CC2=C(CCCC2(C)C)CC1C]

1-(1,2,3,4,5,6,7,8-octahydro-2,3,8,8-tetramethyl-2-naphthyl)ethan-1-one

CAS 54464-57-2

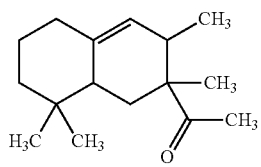 [SMILES: CC(=O)C1(C)CC2C(=CC1C)CCCC2(C)C]

1-(1,2,3,5,6,7,8,8a-octahydro-2,3,8,8-tetramethyl-2-naphthyl)ethan-1-one

CAS 68155-66-8

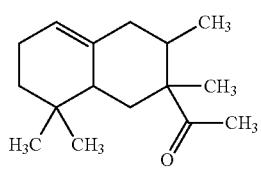 [SMILES: CC(=O)C1(C)CC2C(=CCCC2(C)C)CC1C]

1-(1,2,3,4,6,7,8,8a-octahydro-2,3,8,8-tetramethyl-2-naphthyl)ethan-1-one

CAS 68155-67-9

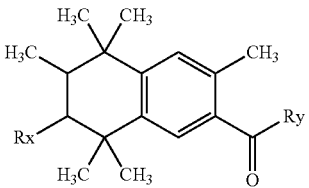

(6S,7S)-3,5,5,6,7,8,8-heptamethyl-6,7-dihydronaphthalene-2-carbaldehyde

Rx is —CH$_3$
Ry is —H
CAS 127459-79-4

1-(3,5,5,6,8,8-hexamethyl-5,6,7,8-tetrahydro-2-naphthalenyl)ethenone

Rx is —H
Ry is —CH3
CAS 21145-77-7

Alicyclic Musks

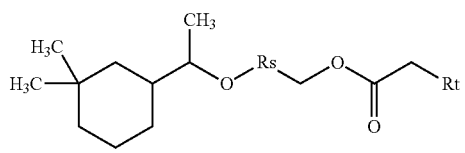

2-[1-(3,3-Dimethylcyclohexyl)ethoxy]-2-methylpropyl propionate

Rs is —C(CH$_3$)$_2$
Rt is —CH$_3$
CAS 141773-73-1

1-(3,3-dimethylcyclohexyl)ethyl 2-acetyloxyacetate

Rs is —C=O
Rt is —H
CAS 236391-76-7

A preferred chemical class of musk substances comprises C$_{14}$-C$_{18}$ macrocyclic lactones.

A preferred musk substance is omega-pentadecalactone of formula (I):

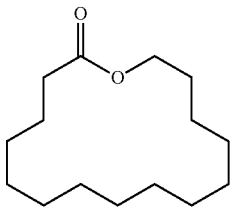

The quantity of musk substance in the composition of this invention depends on the nature of the musk substance. They can be effective at very low levels. Preferably, the proportion of musk substance in the composition is from 0.01% to 2.5%.

The composition of this invention may also comprise further diluents to aid the dissolution of the ingredients of a subsequently-, or previously-applied perfume, provided that the further diluent does not significantly reduce the viscous nature of the composition and its ability to reduce the evaporation of perfume ingredients. A suitable further diluent is an alkyl alcohol such as ethanol.

DETAILED DESCRIPTION OF THE INVENTION

Although the invention is not limited to a particular mechanism, it is believed that the musk substance is causing an effect that has not previously been recognized in the perfume art. Conventionally, it has been thought that musk substances in a perfume aid the diffusivity of the fragrance. We believe, however, that although musk substances do diffuse to reach the nose, they do not increase diffusivity of other perfume ingredients. Instead, the musk substance acts on the olfactory receptors in the nose to increase their sensitivity and thus enhance the perception of fragrance materials. That property therefore operates in conjunction with the retentive nature of the non-scented, viscous, low-volatility, solvent in the present compositions. Thus, the said solvent is present in sufficient quantity to suppress the evaporation of applied perfume, and the musk substance ensures that the nose is able to perceive the fragrance at a strength that is greater than if the musk substance is not present. The knowledge that the musk substance can counteract the retentive property of the viscous low-volatility solvent enables compositions of this invention to be produced, comprising greater than 50% of the said solvent. In this way the compositions of this invention significantly increase the longevity of any applied perfume, whilst still allowing the fragrance to be perceived in the nose at a greater intensity than would otherwise be experienced with the same amount of fragrance material in the absence of the musk substance.

In a further aspect, the present invention provides method for increasing the longevity of a perfume product, which comprises applying a composition of this invention to a substrate prior to, or subsequent to the application of the perfume product to the substrate.

In operation, the composition of this invention is applied to the skin or other substrate prior to, or subsequent to, the application of a perfume product. Preferably the composition of this invention is applied prior to the application of the perfume product.

The method of this invention is particularly suitable where the substrate is human skin. However, the compositions of this invention may also be used on other substrates such as hair, fabrics and household surfaces.

The compositions of this invention may be used to increase the longevity of any perfume product, such as a perfume, eau de toilette, eau de parfum, aftershave, hair spray, skin cream, face cream, sun cream, deodorant, antiperspirant, household cleaning products, including a laundry conditioner, fabric freshener, hard surface cleaner and carpet cleaner. Preferably the perfume product is a perfume.

The invention is illustrated with reference to the following specific example.

Example 1

A composition, designated Formulation 1, was produced using the following ingredients:
83.3% diethyl phthalate
0.05% omega-pentadecalactone
16.65% ethanol Headspace Analysis was used to determine to what extent a perfume lasts longer on the skin, as a result of spraying Formulation 1 in that area first before applying perfume.

1. Overview:
   a) Analysis of the overall volatile profile of the perfume using gas chromatography/mass spectrometry (GC/MS). The sampling technique used is solid-phase microextraction (SPME), which uses a thin fused silica, coated with polymer for the extraction of volatile compounds from the gas phase above a sample. The adsorbed volatile compounds are then thermally desorbed into the injector of the GC/MS.
   b) Identification of key aroma compounds based on GC-MS results and selected compounds for Atmospheric Pressure Chemical Ionization—Mass Spectrometry (APCI-MS) headspace analysis. The analysis occurs many times a second enabling a measure of the abundance of volatile compounds in real time.
   c) Analysis of headspace of perfume alone (Control sample) and perfume with Formulation 1 (Testing sample) at regular time intervals using APCI-MS in Selected Ion Recording (SIR) mode.

2. Materials
   One bottle of perfume and one bottle of Formulation 1 were used for testing.
   Two pieces of A5 Synthetic Leather were used to mimic human skin 3. Sample Preparation Method
   a) Samples for GC-MS Analysis
   10 µL of perfume was added onto 0.1 g of leather, and sealed in an amber bottle (15 ml).
   b) Samples for APCI-MS Analysis
   A blank sample containing just 0.15 g of leather was compared to the control sample, prepared by adding 10 µL of perfume onto 0.15 g of leather.
   To achieve same level of perfume in the testing sample when Formulation 1 was used, a mixture of perfume with Formulation 1 was prepared at 1 to 1 ratio and then 20 µL of this mixture was added onto 0.15 g of leather.
   The above samples were individually placed in a glass duran bottle (100 ml). All samples were kept open at room temperature and then closed with screw lid after 1, 2, 3, 4, 5 and 6 hours.

4. GC-MS Methods
   A trace 1300 series Gas Chromatograph coupled with the Single-Quadrupole Mass Spectrometer (Thermo Fisher Scientific, Hemel Hemptead, UK) was used for analysis of volatile aroma compounds. Samples were heated at 37° C. and a 50/30 µm DVB/CAR/PDMS SPME Fibre (Supelco, Sigma Aldrich, UK) was used to extract volatile aroma compounds from the sample headspace (extraction for 15 min then desorption for 2 min). The inlet temperature was set at 250° C. and a splitless mode was used, and the constant carrier pressure was at 18 psi.
   Separation was carried out on a ZB-WAX Capillary GC Column (length 30 m, inner diameter 0.25 mm, and film thickness 0.25 µm; Phenomenex Inc., Macclesfield, UK).

Column temperature was held initially at 40° C. for 2 min, increased by 6° C./min to 250° C. and held for 5 min. Full scan mode was used to detect the volatile compounds (mass range from 35 to 400 DaAMU).

Volatiles were identified by comparison of each mass spectrum with either the spectra from authentic compounds or with spectra in reference libraries (NIST/EPA/NIH Mass Spectral Library, version 2.0, Faircom Corporation, U.S.).

5. APCI-MS Methods

MS Nose interface (Micromass, Manchester, UK) fitted to a Quattro Ultima mass spectrometer (Waters, Milford, USA) was also known as APCI-MS. It was used for the static headspace analysis of all samples. The headspace was drawn into the APCI-MS source at a rate of 20 mL/min.

The samples were analyzed in Selected Ion Recording (SIR) mode to monitor selected ions of mass to charge (m/z) at 105, 123, 137, 139. The intensity of these ions was measured at cone voltage of 50 V, source temperature of 75° C. and dwell time of 0.5 s.

6. GC-MS Results

A list of the major aroma compounds identified from GC-MS is shown in Table 1.

The same GC-MS method was applied to Formulation 1, and none of the above compounds were identified.

7. Selected Aroma Compounds for APCI-MS Analysis

There were 9 major aroma compounds detected by GC-MS headspace analysis, but not all compounds could be used for APCI-MS analysis because specific compound properties (e.g., volatility, molecular mass, etc.) are required. APCI-MS is a "soft" ionization technique based on proton transfer reaction, which produces mainly molecular ions by the addition of a proton ($H^+$), resulting in the molecular mass plus 1 as APCI ion mass. If the molecule has a hydroxyl group ($OH^-$), they are likely to form water ($H_2O$) and leaves the molecular mass plus 1 minus 18.

A scan method was applied to analyze the headspace of the perfume sample, and the four ions listed in Table 2 showed clear signal and were selected for APCI-MS analysis. The ion mass of 137 could represent both limonene and linalool. The same method was also applied to blank sample (contained leather), but no peaks for any of the four ions were identified.

TABLE 1

| | Retention time (min) | Detected Compound | Molecular Mass (g/mol) |
|---|---|---|---|
| 1 | 6.56 | Limonene | 136 |
| 2 | 11.98 | p-Methylanisole | 122 |
| 3 | 14.57 | Linalool | 154 |
| 4 | 18.10 | Benzylacetate | 150 |
| 5 | 18.90 | Citronellol | 156 |
| 6 | 21.53 | Phenylethyl alcohol | 122 |
| 7 | 22.20 | Hydroxycitronellal | 173 |
| 8 | 23.89 | Hydrocinnamyl alcohol | 136 |
| 9 | 29.12 | Diethyl Phthalate | 222 |

TABLE 2

| APCI-Ion | Compound |
|---|---|
| 105 | Phenylethyl alcohol |
| 123 | p-Methylanisole |
| 137 | Limonene & Linalool |
| 139 | Citronellol |

8. Relative Abundance Measurements

Relative abundance figures for the ions listed in Table 2, at from 1 to 6 hours, are shown in table 3. The relative abundance figures are measured by the current in the detector.

TABLE 3

| | Relative Abundance [All minus background] | | | | | |
|---|---|---|---|---|---|---|
| | 1 hour | 2 hours | 3 hours | 4 hours | 5 hours | 6 hours |
| Perfume alone | | | | | | |
| Citronellol | 54,900 | 42,600 | 19,600 | 15,600 | 15,000 | 9,730 |
| Limonene & Linalool | 3,900,000 | 3,130,000 | 1,290,000 | 967,000 | 665,000 | 462,000 |
| p-Methylanisole | 333,000 | 189,000 | 81,100 | 55,000 | 52,000 | 41,300 |
| Phenylethyl alcohol | 624,000 | 508,000 | 294,000 | 215,000 | 192,000 | 132,000 |
| Total | 4,911,900 | 3,869,600 | 1,684,700 | 1,252,600 | 924,000 | 645,030 |
| Perfume + Formulation 1 | | | | | | |
| Citronellol | 60,900 | 49,600 | 28,500 | 16,500 | 20,700 | 9,280 |
| Limonene & Linalool | 3,640,000 | 3,170,000 | 1,770,000 | 1,430,000 | 1,260,000 | 665,000 |
| p-Methylanisole | 653,000 | 286,000 | 92,600 | 121,000 | 50,300 | 49,400 |
| Phenylethyl alcohol | 461,000 | 361,000 | 220,000 | 228,000 | 323,000 | 119,000 |
| Total | 4,814,900 | 3,866,600 | 2,111,100 | 1,795,500 | 1,654,000 | 842,680 |
| % impact of Formulation 1 | −2% | 0% | 25% | 43% | 79% | 31% |

Thus, it can be seen that a composition according to this invention increases the longevity of a perfume. After 5 hours, 79% more of the volatile aromatic materials are present in the headspace with perfume in the presence of Formulation 1 than with the perfume alone.

What is claimed is:

1. A non-scented composition for application to the skin or other substrate, either prior to, or subsequent to, a perfume, which composition comprises a synthetic compound which exhibits a musk-like odour and at least 70% of the composition comprises a non-scented solvent for perfume ingredients, wherein the solvent has a vapour pressure of less than 0.3 Torr at 25° C., and a viscosity greater than 1 centipoise at 20° C.

2. A composition as claimed in claim 1, for application to the skin or other substrate, which composition increases the intensity of the perfume five hours after application of the perfume by at least 10% compared to the intensity of the perfume in the absence of said composition.

3. A composition as claimed in claim 2, wherein the increase in intensity of the perfume after five hours is at least 50%.

4. A composition as claimed in claim 1, wherein the solvent comprises a chemical compound having both polar and non-polar moieties.

5. A composition as claimed in claim 1, wherein the solvent has a viscosity greater than 5 centipoise at 20° C.

6. A composition as claimed in claim 1, wherein the solvent is diethyl phthalate, isopropyl myristate, monopropylene glycol, or dipropylene glycol.

7. A composition as claimed in claim 6, wherein the solvent is diethyl phthalate.

8. A composition as claimed in claim 1, wherein the musk substance is a $C_{14}$-$C_{18}$ macrocyclic lactone.

9. A composition as claimed in claim 8, wherein the musk substance is omega-pentadecalactone.

10. A composition as claimed in claim 1, wherein the non-scented solvent comprises at least 80% of the composition.

11. A method for increasing the longevity of a perfume product, which comprises applying a composition to a substrate prior to, or subsequent to, the application of the perfume product to the substrate; wherein the composition comprises a natural or synthetic substance which has a musk-like odour; and at least 70% of the composition comprises a non-scented solvent for perfume ingredients, the non-scented solvent having a vapour pressure of less than 0.3 Torr at 25° C., and a viscosity greater than 1 centipoise at 20° C.

12. A method as claimed in claim 11, wherein the substrate is human skin.

13. A method as claimed in claim 11, wherein the composition is applied prior to the application of the perfume product.

14. A method as claimed in claim 11, wherein the perfume product is perfume.

* * * * *